United States Patent
Kim et al.

(10) Patent No.: US 9,170,495 B2
(45) Date of Patent: Oct. 27, 2015

(54) PHENOL MONOMER, POLYMER FOR FORMING A RESIST UNDERLAYER FILM INCLUDING SAME, AND COMPOSITION FOR A RESIST UNDERLAYER FILM INCLUDING SAME

(71) Applicant: DONGJIN SEMICHEM CO., LTD., Incheon (KR)

(72) Inventors: Jeong-Sik Kim, Hwaseong-si (KR); Jae-Woo Lee, Bucheon-si (KR); Jae-Hyun Kim, Seoul (KR)

(73) Assignee: DONGJIN SEMICHEM CO., LTD. (KR)

( * ) Notice: Subject to any disclaimer, the term of this patent is extended or adjusted under 35 U.S.C. 154(b) by 0 days.

(21) Appl. No.: 14/354,978

(22) PCT Filed: Nov. 1, 2012

(86) PCT No.: PCT/KR2012/009111
§ 371 (c)(1),
(2) Date: Apr. 29, 2014

(87) PCT Pub. No.: WO2013/066067
PCT Pub. Date: May 10, 2013

(65) Prior Publication Data
US 2014/0319097 A1    Oct. 30, 2014

(30) Foreign Application Priority Data
Nov. 2, 2011    (KR) .................... 10-2011-0113079

(51) Int. Cl.
| | |
|---|---|
| *G03F 7/11* | (2006.01) |
| *G03F 7/09* | (2006.01) |
| *C08G 61/12* | (2006.01) |
| *C07D 311/86* | (2006.01) |
| *C07D 495/10* | (2006.01) |
| *C07D 491/107* | (2006.01) |
| *C08G 8/20* | (2006.01) |
| *C09D 161/12* | (2006.01) |

(52) U.S. Cl.
CPC .............. *G03F 7/094* (2013.01); *C07D 311/86* (2013.01); *C07D 491/107* (2013.01); *C07D 495/10* (2013.01); *C08G 8/20* (2013.01); *C08G 61/122* (2013.01); *C09D 161/12* (2013.01); *G03F 7/091* (2013.01); *G03F 7/11* (2013.01); *C08G 2261/344* (2013.01)

(58) Field of Classification Search
CPC .. C08G 8/20; C08G 2261/344; C08G 61/122; C07D 311/86; C07D 491/107; C07D 495/10; C09D 161/12
See application file for complete search history.

(56) References Cited

FOREIGN PATENT DOCUMENTS

| EP | 2219076 A1 | 8/2010 |
|---|---|---|
| KR | 10-2009-0046101 A | 5/2009 |
| WO | 2007/007176 A2 | 1/2007 |
| WO | WO 2013/032190 A1 * | 3/2013 |

OTHER PUBLICATIONS

Morgan, P.W. "Aromatic Polyesters with Large Cross-Planar Substituents". Macromolecules, Vo. 3, No. 5, Sep.-Oct. 1970, pp. 536-544.*
Zhang et al., Polymer Chemistry, 2010 published on the web on Jan. 11, 2010, vol. 1, pp. 485-493. which is Journal of the Royal Society of Chemistry.*
Chen et al., Journal of Applied Polymer Science, vol. 27, (1982), pp. 3289-3312.*
Sen et al abstract CAN 25:3709 from CAPLUS of Journal of the Indian Chemical Society (1930), 7, 997-1006, the abstract has 2 pages present.*
Written Opinion of the International Searching Authority, PCT/KR2012/009111, May 6, 2013.
Tseng, Ya-Hsien et al., Stable Organic Blue-Light-Emitting Devices Prepared from Poly[spiro(fluorene-9,9'-xanthene)], Macromolecules, 2005, vol. 38, No. 24, pp. 10055-10060.
Zhang, Shu-Jiang et al., High organosolubility and optical transparency of novel polyimides derived from 2',7'-bis(4-amino-2-trifluoromethylphenoxy)-spiro(fluorene-9,9'-xanthene), Materials Chemistry and Physics, Aug. 15, 2011, vol. 128, Issue 3, pp. 392-399.
International Search Report, PCT/KR2012/009111, WIPO, Mar. 28, 2013.

* cited by examiner

*Primary Examiner* — Cynthia Hamilton
(74) *Attorney, Agent, or Firm* — Park & Associates IP Law, P.C.

(57) ABSTRACT

A phenolic monomer used in the lithographic process for semiconductor fabrication, a polymer for preparing a resist under-layer comprising the same, and a resist under-layer composition comprising the same, are disclosed. The phenolic monomer is represented by the formula 1 of the specification, in Formula 1, R1, R2, R3, and R4 are independently a hydrogen atom, or a straight-chain, branched, monocyclic or polycyclic saturated or unsaturated hydrocarbon group having 1 to 20 carbon atoms with or without a hetero atom; A is a monocyclic or polycyclic aromatic hydrocarbon group having 4 to 20 carbon atoms; X is an oxygen atom (O) or a sulfur atom (S); and Y is a single bond, a methylene group (—CH2—), an oxygen atom (O), a sulfur atom (S), an amino group (—NH—), or two isolated hydrogen atoms, wherein A, R1, R2, R3, and R4 can be substituted with a straight-chain, branched, monocyclic or polycyclic saturated or unsaturated hydrocarbon group having 1 to 20 carbon atoms with or without a hetero atom; and either R1 and R2 or R3 and R4 are independently linked to each other to form a ring.

11 Claims, 2 Drawing Sheets

PHENOL MONOMER, POLYMER FOR FORMING A RESIST UNDERLAYER FILM INCLUDING SAME, AND COMPOSITION FOR A RESIST UNDERLAYER FILM INCLUDING SAME

REFERENCE TO RELATED APPLICATIONS

This application is a U.S. National Phase application of International Application No. PCT/KR2012/009111 filed on Nov. 1, 2012, which designates the United States and claims priority of Korean Patent Application No. 10-2011-0113079 filed on Nov. 2, 2011, the entire contents of which are incorporated herein by reference.

FIELD OF THE INVENTION

The present invention relates to a phenolic monomer, a polymer for preparing a resist under-layer comprising the same, and a resist under-layer composition comprising the same and, more particularly to a phenolic monomer used in the lithographic process for semiconductor fabrication, a polymer for preparing a resist under-layer comprising the same, and a resist under-layer composition comprising the same.

BACKGROUND OF THE INVENTION

With a tendency towards the reduction in the size of patterns pertaining to miniaturization and integration of semiconductor devices, the photoresist layer and the patterns are getting thinner in order to prevent collapse of the photoresist pattern. The use of the thin photoresist pattern makes it difficult to etch a target layer, so an inorganic or organic layer with high etching resistance is provided between the photoresist pattern and the target layer to be etched. Such a layer is called "(resist) under-layer" or "hard mask", and a process for patterning an under-layer using a photoresist pattern and then etching a target layer using the under-layer pattern is called "(resist) under-laying process". The inorganic under-layer used in the under-laying process is composed of silicon nitride, silicon oxynitride, polysilicon, titanium nitride, amorphous carbon, and so forth, and typically prepared by the chemical vapor deposition (CVD) method. The under-layer produced by the chemical vapor deposition (CVD) method is excellent in etching selectivity and etching resistance but problematic in regard to particles or initial facility investment as required. To solve these problems, there has been studied on an organic under-layer that can be prepared by spin coating as a substitute for the under-layer prepared by deposition.

A multilayer resist comprising the organic under-layer typically has a dual-layer structure (using dual-layer resist technique) or a triple-layer structure (using triple-layer resist technique). For a resist having a dual-layer structure, the over-layer is a photoresist layer capable of pattern implementation, and the resist under-layer is a hydrocarbon layer available to the etching process using oxygen gas. The resist under-layer is supposed to play a role as a hard mask in etching an underlying substrate, so it is required to have high etching resistance and to consist of hydrocarbon alone containing substantially none of silicon atom in case of etching using oxygen gas. Further, the resist under-layer is needed to have a function as a layer for preventing scattered reflection of light source in order to control the standing wave of the overlying resist film and avoid collapse of the pattern when using a KrF or ArF light source. More specifically, it is necessary to control the reflection from the under-layer onto the resist over-layer.

For a resist having a triple-layer structure, an inorganic hard mask intermediate layer (i.e., a second under-layer composed of an inorganic substance) is further provided between the over-layer (i.e., a photoresist layer) and the resist under-layer (i.e., a first under-layer composed of a hydrocarbon compound). The second under-layer can be a silicon oxide layer, a silicon nitride layer, or a silicon oxynitride (SiON) layer as prepared by the chemical vapor deposition (CVD) method at high temperature. Preferably, the second under-layer can be a SiON layer which is highly effective as a bottom anti-reflective coating layer. The thickness of the second under-layer is 5 to 200 nm, preferably 10 to 100 nm. The resist under-layer (i.e., the first under-layer) is required to have thermal resistance at a temperature of 240 to 500° C., because the substrate is heated up to 240 to 500° C. in order to form the second under-layer (particularly, the SiON layer) on the resist under-layer. However, when the resist under-layer does is not resistant to such a high temperature, it is potentially susceptible to decomposition to contaminate the inside of the equipment during preparation of the inorganic hard mask intermediate layer (i.e., the second under-layer).

SUMMARY OF THE INVENTION

It is therefore an object of the present invention to provide a phenolic monomer having high transparency, high thermal resistance, low reflection, and low shrinkage; a polymer for preparing a resist under-layer that comprises the monomer and has characteristics, such as high transparency, high thermal resistance, low reflection, and low shrinkage, and excellences in cross-linking property and etching resistance; a resist under-layer composition comprising the polymer; and a patterning method using the resist under-layer composition.

It is another object of the present invention to provide a phenolic monomer having a self-crosslinking property at high temperature and being capable of functioning as an organic bottom anti-reflective coating layer; a resist under-layer composition comprising the polymer; and a patterning method using the resist under-layer composition.

It is still another object of the present invention to provide a phenolic monomer, a polymer for preparing a resist under-layer comprising the same, a resist under-layer composition comprising the same, and a patterning method using the same, where the resist under-layer not only has high etching resistance but also realizes good smoothness when deposited on a patterned wafer having a height difference.

In order to achieve these objects, the present invention provides a phenolic monomer represented by the following formula 1:

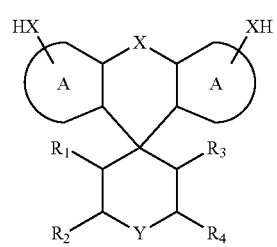

Formula 1 wherein R1, R2, R3, and R4 are independently a hydrogen atom, or a straight-chain, branched, monocyclic or polycyclic saturated or unsaturated hydrocarbon group having 1 to 20 carbon atoms with or without a hetero atom; A is a monocyclic or polycyclic aromatic hydrocarbon group having 4 to 20 carbon atoms; X is an oxygen atom (O) or a sulfur atom (S); and Y is a single bond, a methylene group (—CH2-), an oxygen atom (O), a sulfur atom (S), an amino group (—NH—), or two isolated hydrogen atoms, wherein A, R1, R2, R3, and R4 can be substituted with a straight-chain, branched, monocyclic or polycyclic saturated or unsaturated hydrocarbon group having 1 to 20 carbon atoms with or without a hetero atom; and either R1 and R2 or R3 and R4 are independently linked to each other to form a ring.

The present invention provides a polymer for preparing a resist under-layer, comprising a repeating unit represented by the following formula 2:

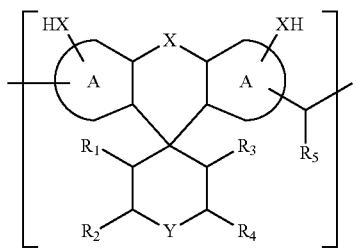

Formula 2

Wherein R1, R2, R3, and R4 are the same as defined in Formula 1, R5 is a hydrogen atom, or a straight-chain, branched, monocyclic or polycyclic saturated or unsaturated hydrocarbon group having 1 to 20 carbon atoms with or without a hetero atom.

The present invention provides a polymer for preparing a resist under-layer, the polymer comprising a repeating unit represented by the formula 2; and an organic solvent.

The phenolic monomer of the present invention has high transparency, high thermal resistance, low reflection, and low shrinkage. The polymer for preparing a resist under-layer as obtained by polymerization of the phenolic monomer has the same characteristics of the phenolic monomer, such as high transparency, high thermal resistance, low reflection, and low shrinkage, and excellences in cross-linking property and etching resistance. Further, the resist under-layer composition comprising the phenolic polymer forms a hard mask (i.e., a spin-on-carbon (SOC) hard mask) by spin coating, exerts the self-crosslinking property without an additive such as a cross-linking agent at high temperature (e.g., 350 to 400° C.) and has a low out-gassing rate in the subsequent step of heating up to 400° C., consequently with usefulness as a high-temperature SOC material. Furthermore, the under-layer formed by the present invention not only functions as an organic bottom anti-reflective coating layer but secures good gap-filling performance and good smoothness when applied onto a wafer having a height difference.

DETAILED DESCRIPTION OF THE INVENTION

Figure 1:
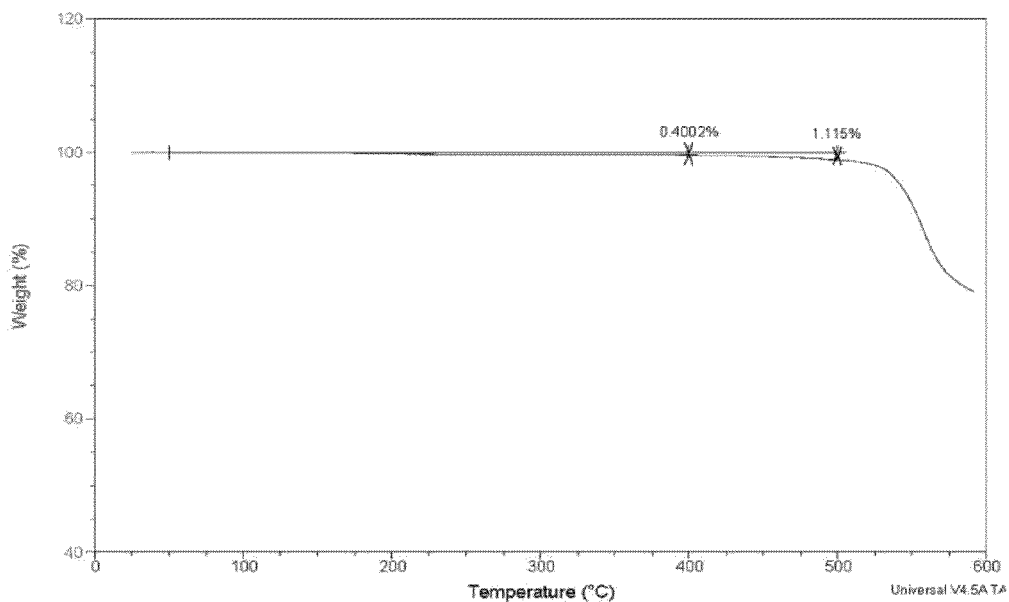
FIGS. 1 and 2 are thermogravimetric (TGA) graphs of under-layer samples according to Example 1 of the present invention and Comparative Example 1, respectively.

The present invention provides a (thio)phenolic monomer represented by the following formula 1:

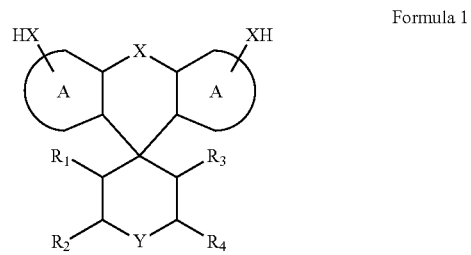

Formula 1

In the formula 1, R1, R2, R3, and R4 are independently a hydrogen atom, or a straight-chain, branched, monocyclic or polycyclic saturated or unsaturated hydrocarbon group having 1 to 20 carbon atoms with or without a hetero atom, such as an halogen atom (e.g., F, Cl, Br, or I), an oxygen atom (O), or a sulfur atom (S); A is a monocyclic or polycyclic aromatic hydrocarbon group having 4 to 20 carbon atoms; X is an oxygen atom (O) or a sulfur atom (S); and Y is a single bond (forming a five-membered ring, a methylene group (—CH2-), an oxygen atom (O), a sulfur atom (S), an amino group (—NH—), or two isolated hydrogen atoms (not forming a ring). In this regard, A, R1, R2, R3, and R4 can be substituted with a straight-chain, branched, monocyclic or polycyclic saturated or unsaturated hydrocarbon group having 1 to 20 carbon atoms with or without a hetero atom, such as an halogen atom (e.g., F, Cl, Br, or I), an oxygen atom (O), or a sulfur atom (S); and either R1 and R2 or R3 and R4 are independently linked to each other to form a ring (e.g., a benzene ring, a naphthalene ring, an anthracene ring, etc.).

The phenolic monomer represented by the formula 1 can be prepared, as shown in the following reaction scheme 1, by the dehydration of a ketone or thioketone derivative represented by the formula A and a diol or dithiol compound represented by the formula B in the presence of a general acid catalyst.

Reaction Scheme 1

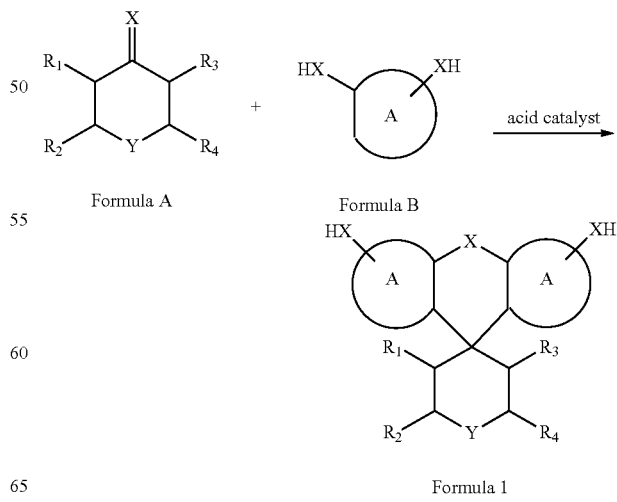

Formula 1

In the reaction scheme 1, A, R1, R2, R3, R4, X, and Y are as defined in the formula 1.

In the preparation of the phenolic monomer, the content ratio of the ketone or thioketone derivative of the formula A and the diol or dithiol compound of the formula B is controlled so that the diol or dithiol compound is used in an amount of 2 to 10 equivalents, preferably 2.1 to 4 equivalents, more preferably 2.2 to 2.5 equivalents, with respect to one equivalent of the ketone or thioketone derivative. When the content of the diol or dithiol compound is less than 2 equivalents with respect to one equivalent of the thioketone derivative, the synthesis yield of the monomer abruptly decreases. The content of the diol or dithiol compound being greater than 10 equivalents with respect to one equivalent of the thiolketone derivative makes it difficult to remove unreacted chemicals, and the remaining chemicals possibly cause side reactions during the polymerization reaction and deteriorate the properties of the monomer and the polymer, such as high thermal resistance, high etching resistance, low shrinkage, or the like.

The unlimited examples of ketone or thioketone derivatives represented by Formula A include

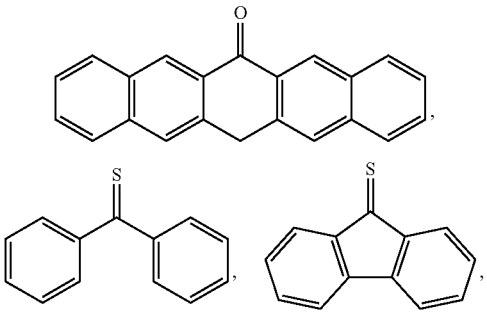

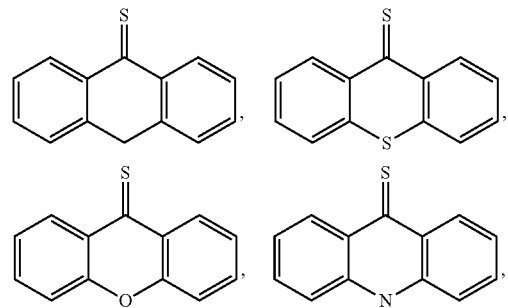

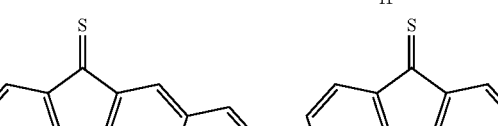

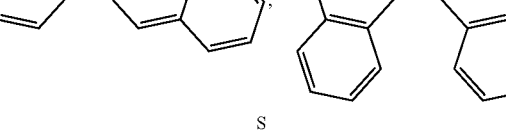

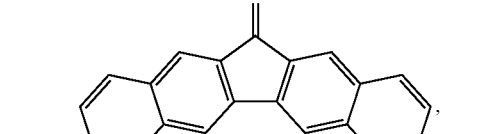

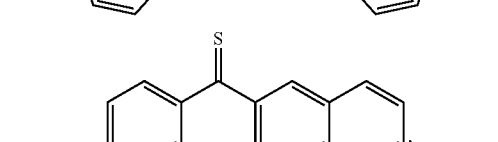

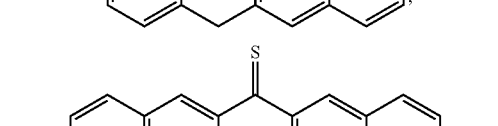

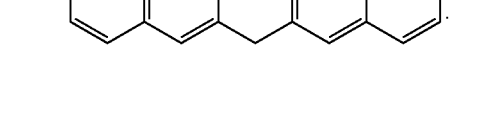

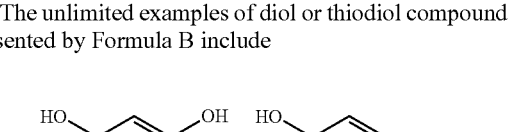

The unlimited examples of diol or thiodiol compound represented by Formula B include

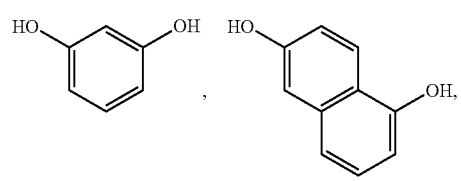

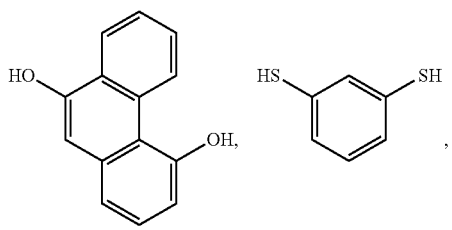
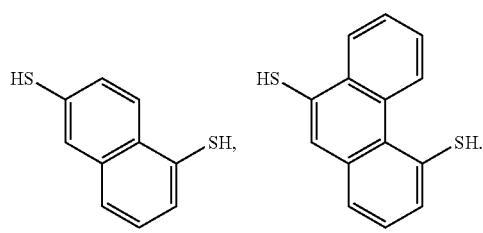
The unlimited examples of phenolic monomer represented by Formula 1 include
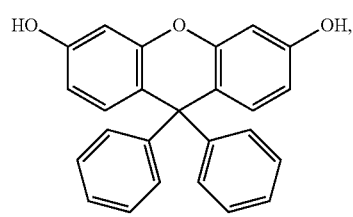
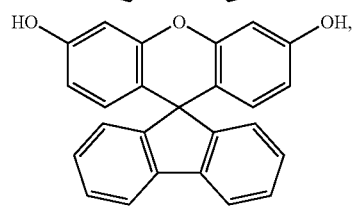
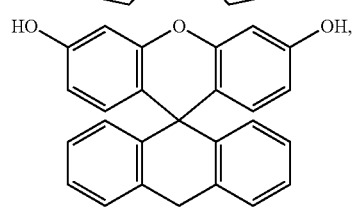
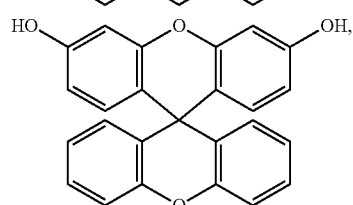
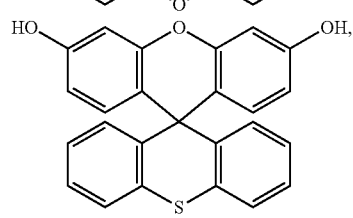
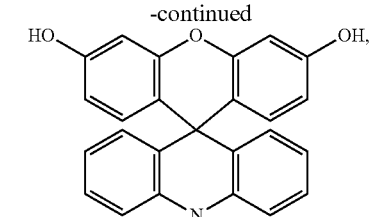
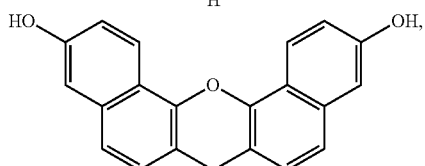
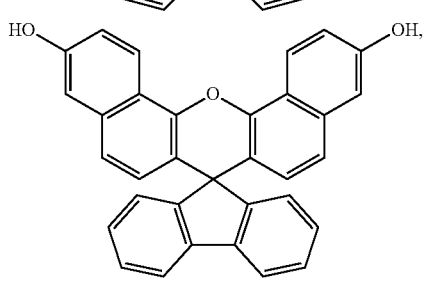
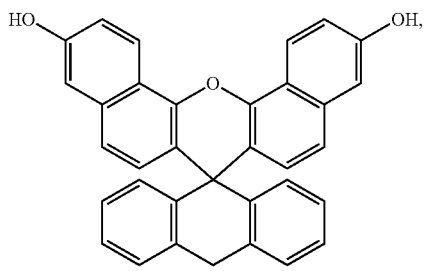
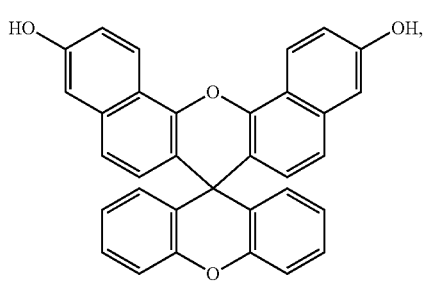
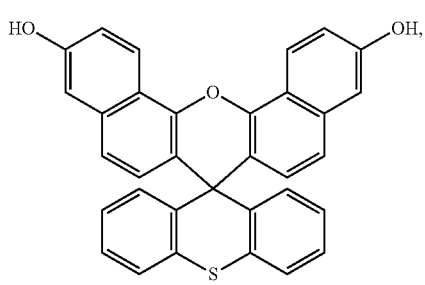

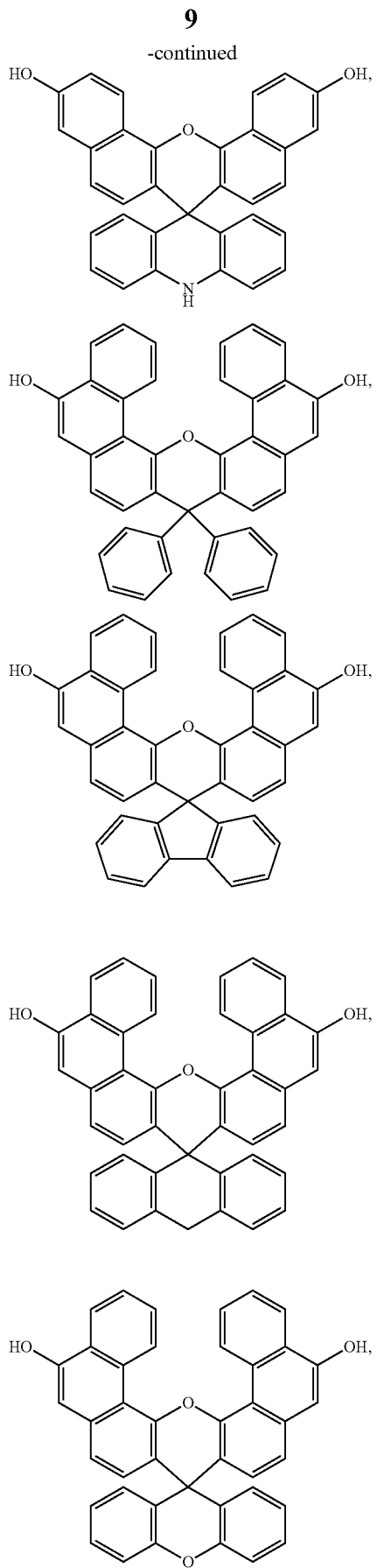
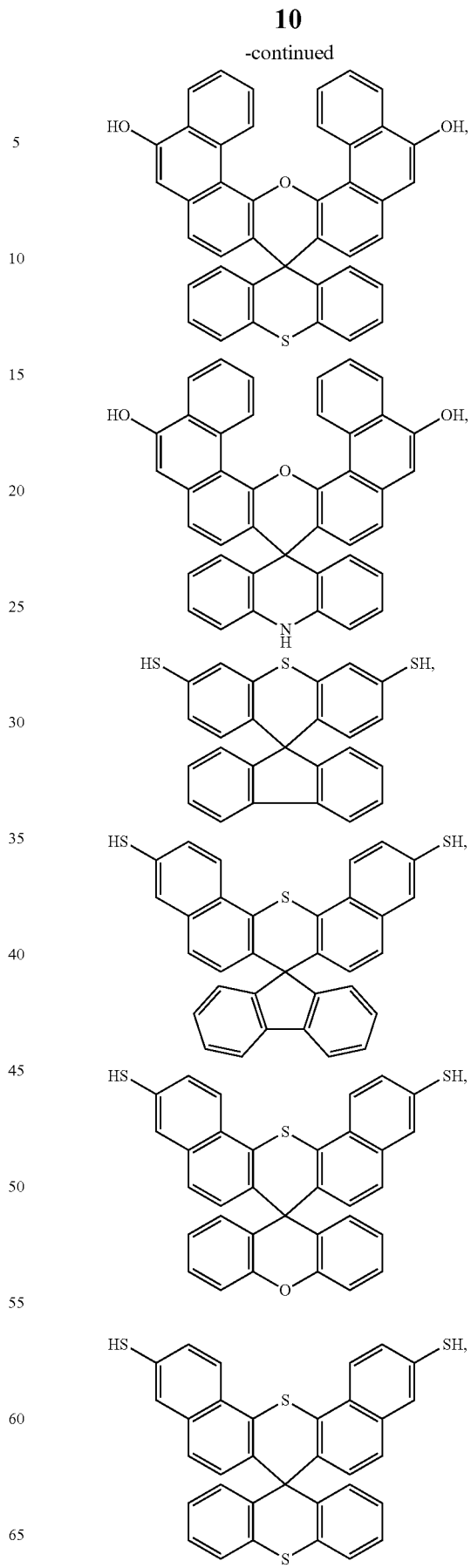

-continued

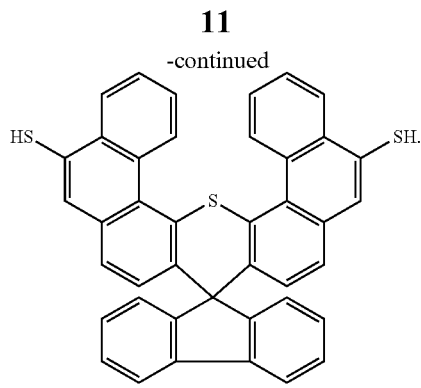

The polymer for preparing a resist under-layer according to the present invention is positioned between the substrate to be etched and the photoresist layer and used to form a resist under-layer (functioning as a hard mask) for etching the substrate into a defined pattern. The polymer comprises a repeating unit of the following formula 2.

Formula 2

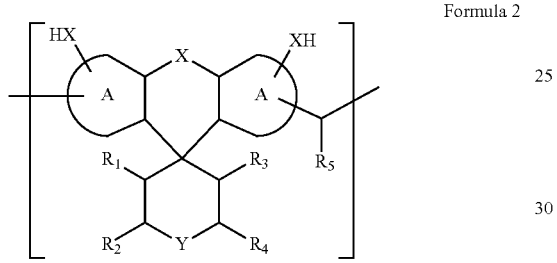

In the formula 2, A, R1, R2, R3, R4, X, and Y are as defined in the formula 1; and R5 is a hydrogen atom, or a straight-chain, branched, monocyclic or polycyclic saturated or unsaturated hydrocarbon group having 1 to 20 carbon atoms with or without a hetero atom, such as a halogen atom (e.g., F, Cl, Br, or I), an oxygen atom (O), or a sulfur atom (S).

The unlimited examples of polymer for preparing a resist under-layer, comprising a repeating unit of the formula 2 include polymers containing the repeating unit represented by following Formula 2a to 2q.

Formula 2a

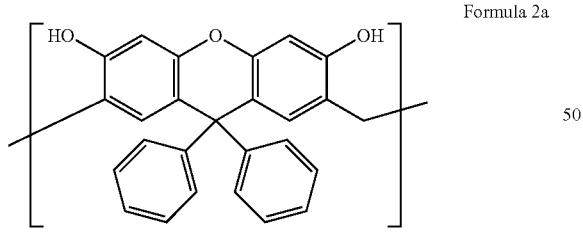

Formula 2b

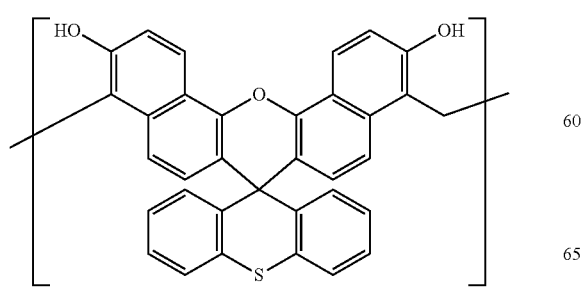

Formula 2c

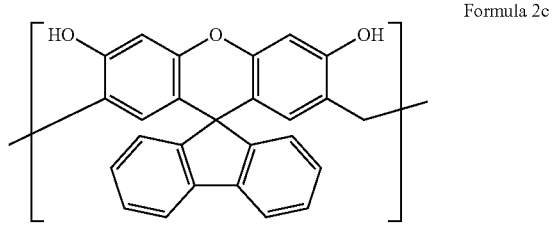

Formula 2d

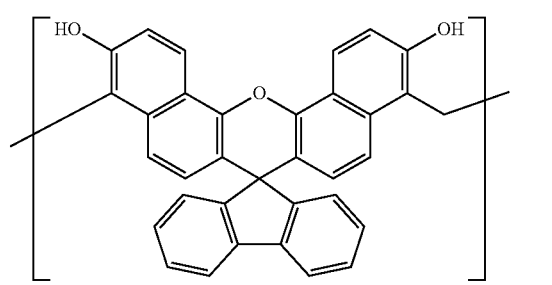

Formula 2e

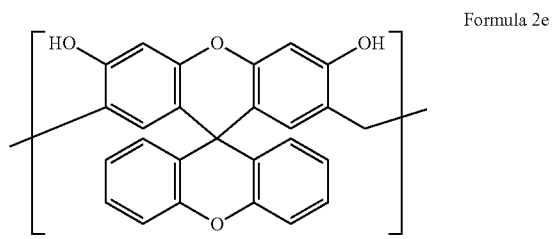

Formula 2f

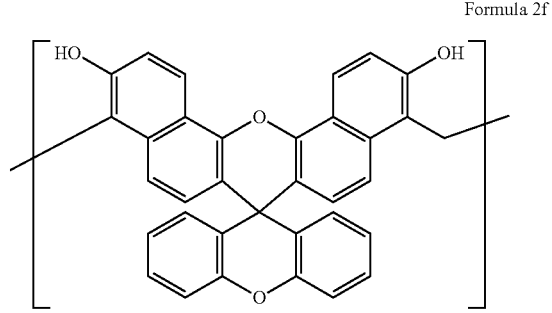

Formula 2g

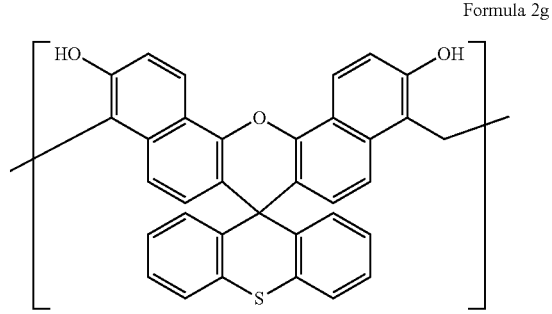

-continued
Formula 2h
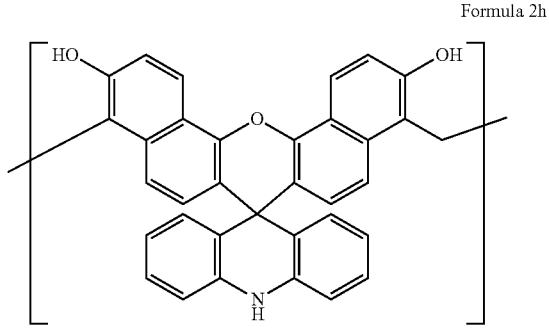
Formula 2i
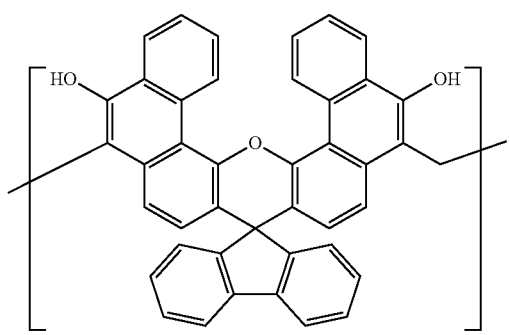
Formula 2j
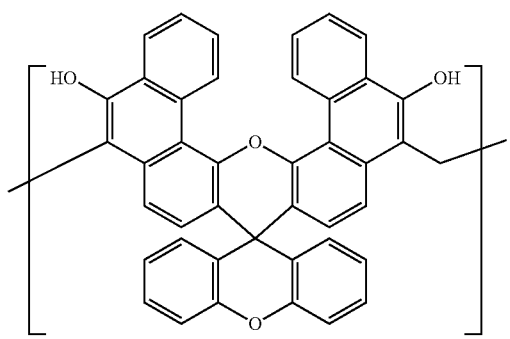
Formula 2k
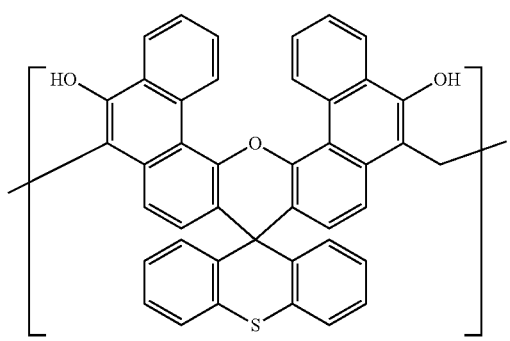
Formula 2l
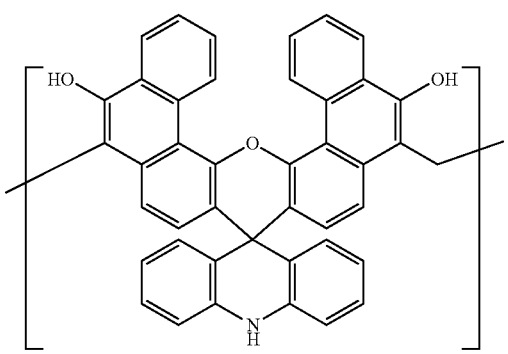
Formula 2m
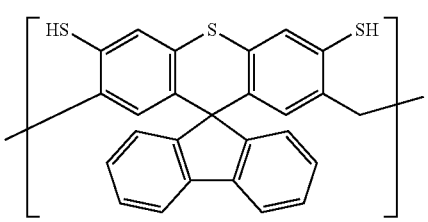
Formula 2n
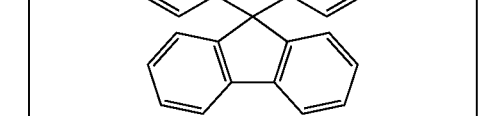
Formula 2o
Formula 2p
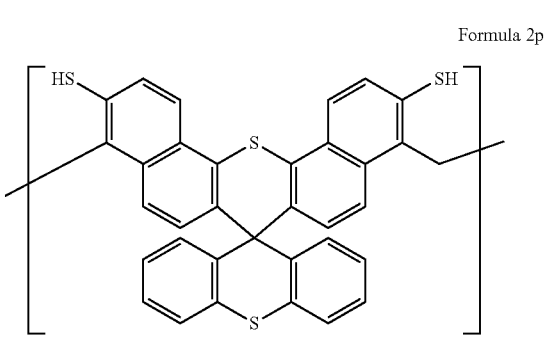

-continued

Formula 2q

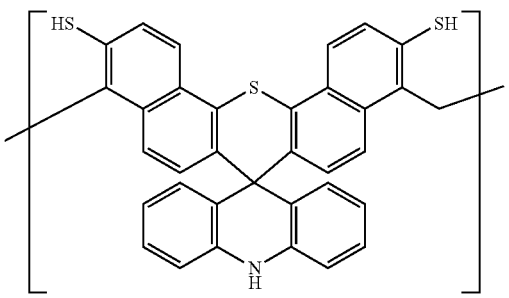

The polymer for preparing a resist under-layer that comprises a repeating unit of the formula 2 can be obtained by the condensation reaction of a phenolic monomer of the formula 1 and an aldehyde in the presence of an acid catalyst. The aldehyde as used herein may be any kind of aldehydes containing the substituent R5 of the formula 2. The specific examples of the aldehyde include formaldehyde, benzaldehyde, acetaldehyde, and so forth. The preferred aldehyde is formaldehyde. A polymer of the same structure can be obtained using paraformaldehyde instead of formaldehyde. In the preparation of the polymer, the content ratio of the phenolic monomer of the formula 1 and the aldehyde is controlled so that the aldehyde is used in an amount of 0.5 to 5 equivalents, preferably 0.55 to 3 equivalents, more preferably 0.6 to 2 equivalents, with respect to one equivalent of the phenolic monomer. When the content of the aldehyde is greater than 5 equivalents with respect to one equivalent of the phenolic monomer, the molecular weight is abruptly increased and becomes uncontrollable. The content of the aldehyde less than 0.5 equivalent with respect to one equivalent of the phenolic monomer leads to an extremely low molecular weight, consequently with a failure to obtain a desired polymer. The acid catalyst used in the condensation reaction may be any kind of known acid catalyst, such as, for example, nitric acid, sulfuric acid, formic acid, oxalic acid, acetic acid, methane sulfonic acid, camper sulfonic acid, p-toluene sulfonic acid, trifluoromethane sulfonic acid, and so forth. An extremely strong acid makes it difficult to control the molecular weight of the polymer, whereas an extremely weak acid leads to an extremely low molecular weight, consequently with a failure to obtain a desired polymer, and increases the reaction time. In the preparation of the polymer, the content of the acid catalyst is 0.002 to 0.02 equivalent, preferably 0.005 to 0.010 equivalent, with respect to one equivalent of the phenolic monomer. The content of the acid catalyst greater than 0.02 equivalent with respect to one equivalent of the phenolic monomer potentially makes it difficult to control the molecular weight of the polymer, whereas the content of the acid catalyst less than 0.002 equivalent potentially leads to a failure to obtain a desired polymer.

The weight average molecular weight Mw of the polymer for preparing a resist under-layer that comprises a repeating unit of the formula 2 is, for example, 500 to 20,000, preferably 700 to 8,000, more preferably 2,000 to 4,000. The weight average molecular weight Mw of the polymer greater than 20,000 leads to a failure to conduct a gap-filling process when applying the polymer to the pattern having a height difference, and causes a flexion along the profile of the height difference of the pattern, consequently with poor smoothness. The weight average molecular weight Mw of the polymer less than 500 deteriorates coatability, thermal resistance, etching resistance, or the like.

The resist under-layer composition of the present invention, which is used to form an under-layer on the substrate by a spin coating method or a spin-on-carbon method, comprises the polymer for preparing a resist under-layer, and an organic solvent.

The organic solvent used in the present invention is not specifically limited and may be any kind of organic solvent for under-layer that is soluble to the polymer for preparing a resist under-layer. The specific examples of the organic solvent as used herein may include propylene glycol monomethyl ether acetate (PGMEA), propylene glycol monomethyl ether (PGME), cyclohexaneone (CH), ethyl lactate (EL), gamma-butyrolactone (GBL), or mixtures of thereof.

In the resist under-layer composition, the content of the polymer for preparing a resist under-layer is 1 to 25 wt. %, preferably 3 to 20 wt. %, more preferably 4 to 16 wt. %. The content of the organic solvent is the remainder other than the solid portion such as the polymer for preparing a resist under-layer. The content of the polymer less than 1 wt. % is too insignificant to form an under-layer (i.e., resist under-layer), whereas the content of the polymer greater than 25 wt. % is too excessive to uniformly form an under-layer.

Under necessity, the resist under-layer composition of the present invention may further comprise an additive, such as a cross-linking agent, a surfactant, an acid generator, and so forth.

The cross-linking agent, which is to induce a cross-linking reaction and harden the under-layer, may be any kind of general cross-linking agent, either melamine type or epoxy type. The specific examples of the cross-linking agent may include MX-270®, MX-280®, or MX-390® commercially available from Mitsubishi Chemicals Co., Ltd.; or 2-{[4-2(2-oxyranylmethoxy)phenoxy]methyl}oxirane. If any, the content of the cross-linking agent is 1 to 20 parts by weight, preferably 3 to 15 parts by weight, with respect to 100 parts by weight of the polymer for preparing a resist under-layer. The content of the cross-linking agent less than 1 part by weight with respect to 100 parts by weight of the polymer for preparing a resist under-layer is too insignificant to acquire a sufficiently high degree of cross-linking. The content of the cross-linking agent greater than 20 parts by weight potentially leads to deterioration in the stability of the resist.

The acid generator can be added in order to lower the cross-linking temperature of the polymer and enhance the degree of cross-linking. The acid generator as used herein may be a photoacid generator or a thermal acid generator. Under circumstances, an acid may be used as the acid generator. A thermal acid generator which is superior in catalytic efficiency at high temperature can be used rather than a photoacid generator. The specific examples of the thermal acid generator as used herein are TAG®-series manufactured by King Industry Co., Ltd. The content of the acid generator is 5 parts by weight or less, preferably 1 to 4 parts by weight, with respect to 100 parts by weight of the polymer for preparing a resist under-layer. The content of the acid generator greater than 5 parts by weight with respect to 100 parts by weight of the polymer for preparing a resist under-layer may deteriorate the stability of the resist.

The surfactant can be used to improve coating failures occurring due to an increased content of the solid portion in the preparation of a resist under-layer. The specific examples of the surfactant commercially available are SULFINOL®-series manufactured by Jane Air Product Co., Ltd., or F-series (e.g., F-410, F-444, F-477, R-08, or R-30) manufactured by DIC Co., Ltd. If any, the content of the surfactant is 0.1 to 1 part by weight, preferably 0.2 to 0.8 part by weight, with respect to 100 parts by weight of the resist under-layer composition. The content of the surfactant greater than 1 part by weight with respect to 100 parts by weight of the resist under-layer potentially may deteriorate the quality of the resist layer.

The present invention also provides a patterning method using the resist under-layer composition. More specifically, the patterning method comprises: (a) forming a resist under-layer on the top of a substrate to be etched (e.g., a silicon wafer with an overlying aluminum layer), by using the resist under-layer composition of the present invention; (b) forming a photoresist layer on the top of the resist under-layer; (c) exposing the photoresist layer to a radioactive radiation into a defined pattern to form a pattern having an exposed region in the photoresist layer; (d) selectively removing the photoresist layer and the resist under-layer according to the pattern to expose the substrate in accordance with the pattern; and (e) etching the exposed portion of the substrate. Under necessity, prior to the step (b), the patterning method may further comprise a step of forming a general silicon-containing resist under-layer (i.e., an inorganic under-layer) and/or a bottom anti-reflective coating (BARC) layer.

The step of forming the resist under-layer may comprise: applying the resist under-layer composition of the present invention on the top of the substrate in a thickness of 500 to 6,000 Å by spin coating; and heating at 240 to 400° C., preferably 350 to 400° C. for 50 to 180 seconds. The resist under-layer thus obtained has a thickness of 40 to 550 nm. The heating temperature below 240° C. lowers the degree of cross-linking to deteriorate the etching resistance of the resist, whereas the heating temperature above 400° C. renders the polymer decomposed to contaminate the inside of the equipment. The patterning of the photoresist layer can be carried out by development using an aqueous alkali solution, such as a TMAH developer. The removal of the resist under-layer can be carried out by dry etching with a CHF3/CF4 mixed gas. And, the substrate can be etched by plasma etching using a Cl2 or HBr gas. In this regard, the etching conditions, such as the thickness of the resist under-layer, the heating temperature and time, and the etching method are not specifically limited to the above specifications and may be varied according to the conditions of the process.

The resist under-layer of the present invention is prepared from a polymer for preparing a resist under-layer as obtained by the polymerization of a phenolic monomer having high transparency, high thermal resistance, low reflection, and low shrinkage. The polymer has such characteristics as high transparency, high thermal resistance, low reflection, and low shrinkage, and excellences in cross-linking property and etching resistance. Further, the resist under-layer composition comprising the polymer forms a hard mask (i.e., a spin-on-carbon (SOC) hard mask) by spin coating, exerts the self-crosslinking property without an additive such as a cross-linking agent at high temperature (e.g., 350 to 400° C.) and has a low out-gassing rate in the subsequent step of heating up to 400° C., consequently with usefulness as a high-temperature SOC material. Furthermore, the resist under-layer formed by the present invention not only functions as an organic bottom anti-reflective coating layer but secures high gap-filling performance and good smoothness when applied on a wafer having a height difference.

Hereinafter, the present invention will be described in further detail by way of the following examples, which are given for illustrations only and not intended to limit the scope of the present invention.

Synthesis Example 1

Synthesis of Polymer Comprising Repeating Unit of Formula 2a 30 g (0.165 mole) of benzophenone and 40 g (0.362 mole) of resorcinol were put into a 0.5 L two-neck round-bottomed flask. 161.5 g of sulfuric acid as an acid catalyst was added to the mixture. A reflux condenser was attached to the flask, and the mixture was stirred at 120° C. for 12 hours. After completion of the stirring, the reaction flask was cooled down to 0° C. and agitated for 3 hours while 300 g of an ice water was slowly added. The solid product thus obtained was dispersed. Then, the dispersed product was filtered out and washed with distilled water until the filtrate became neutral (pH 7). The product was dried out in a vacuum oven at 80° C. for 8 hours to obtain 53.7 g (89.0% yield) of a phenolic monomer. 50 g (0.136 mole) of the vacuum-dried monomer and 0.61 g (0.007 mole) were put into a 0.5 L 3-neck round-bottomed flask. 137.2 g of ethyl lactate was dissolved in the mixture, and a reflux condenser was attached to the flask. The flask was then heated up to 90° C. under agitation. 22.15 g (0.273 mole) of 37% formalin (i.e., aqueous formaldehyde solution) was slowly added to the flask under agitation for one hour, and the mixture was heated up to 100° C. and stirred for 12 more hours. After completion of the stirring, the reactant solution was cooled down to the room temperature and slowly added dropwise to a mixed solvent of methanol and water to precipitate a polymer. The polymer precipitate was filtered out, washed with the same solvent three times, and dried out in a vacuum oven at 80° C. for 48 hours to obtain 43.8 g (84.8% yield) of a polymer comprising a repeating unit of the formula 2a. The polymer thus obtained was then measured in regard to the weight average molecular weight Mw and the polydispersity (PD) using gel permeation chromatography (GPC) (Mw=3,500, PD=1.87).

Synthesis Example 2

Synthesis of Polymer Comprising Repeating Unit of Formula 2b

The procedures were performed in the same manner as described in Synthesis Example 1, excepting that 48.34 g (0.302 mole) of 1,6-dihydroxynaphthalene in combination with 134.56 g (1.372 mole) of sulfuric acid as an acid catalyst was used rather than 40 g (0.362 mole) of resorcinol to prepare 56.4 g (88.1% yield) of a monomer, and that 50 g (0.107 mole) of the monomer, 0.48 g (0.005 mole) of oxalic acid, 17.4 g (0.214 mole) of 37% formalin, and 132.8 g of ethyl lactate were used to obtain 44.5 g of a polymer comprising a repeating unit of formula 2b (86.8% yield, Mw=3,200, PD=1.95).

Synthesis Example 3

Synthesis of Polymer Comprising Repeating Unit of Formula 2d

The procedures were performed in the same manner as described in Synthesis Example 1, excepting that 30 g (0.141 mole) of 9-fluorenone and 49.82 g (0.311 mole) of 1,6-dihydroxynaphthalene in combination with 138.67 g (1.414 mole) of sulfuric acid as an acid catalyst were used rather than 30 g (0.165 mole) of benzophenone and 40 g (0.362 mole) of resorcinol to prepare 59.8 g (91.1% yield) of a monomer, and that 55 g (0.118 mole) of the monomer, 0.53 g (0.006 mole) of oxalic acid, 19.22 g (0.237 mole) of 37% formalin, and 146.2 g of ethyl lactate were used to obtain 51.2 g of a polymer comprising a repeating unit of formula 2d (90.7% yield, Mw=2,800, PD=1.74).

Synthesis Example 4

Synthesis of Polymer Comprising Repeating Unit of Formula 2e

The procedures were performed in the same manner as described in Synthesis Example 1, excepting that 30 g (0.153 mole) of xanthone in combination with 37.04 g of resorcinol and 138.67 g (1.414 mole) of sulfuric acid as an acid catalyst was used rather than 30 g (0.165 mole) of benzophenone to prepare 51.2 g (88.0% yield) of a monomer, and that 50 g (0.131 mole) of the monomer, 0.59 g (0.007 mole) of oxalic acid, 21.34 g (0.263 mole) of 37% formalin, and 136.5 g of ethyl lactate were used to obtain 46.5 g of a polymer comprising a repeating unit of formula 2e (90.2% yield, Mw=3,100, PD=1.82).

Synthesis Example 5

Synthesis of Polymer Comprising Repeating Unit of Formula 2f

The procedures were performed in the same manner as described in Synthesis Example 1, excepting that 30 g (0.153 mole) of xanthone and 53.88 g (0.336 mole) of 1,6-dihydroxynaphthalene in combination with 149.97 g (1.372 mole) of sulfuric acid as an acid catalyst were used rather than 30 g (0.165 mole) of benzophenone and 40 g (0.362 mole) of resorcinol to prepare 67.2 g (91.5% yield) of a monomer, and that 60 g (0.125 mole) of the monomer, 0.56 g (0.006 mole) of oxalic acid, 20.27 g (0.263 mole) of 37% formalin, and 158.8 g of ethyl lactate were used to obtain 55.1 g of a polymer comprising a repeating unit of formula 2f (89.6% yield, Mw=3,100, PD=1.82).

Synthesis Example 6

Synthesis of Polymer Comprising Repeating Unit of Formula 2 g

The procedures were performed in the same manner as described in Synthesis Example 1, excepting that 30 g (0.141 mole) of thioxanthone and 49.80 g (0.311 mole) of 1,6-dihydroxynaphthalene in combination with 138.62 g (1.413 mole) of sulfuric acid as an acid catalyst were used rather than 30 g (0.165 mole) of benzophenone and 40 g (0.362 mole) of resorcinol to prepare 62.7 g (89.3% yield) of a monomer, and that 60 g (0.121 mole) of the monomer, 0.54 g (0.006 mole) of oxalic acid, 19.61 g (0.242 mole) of 37% formalin, and 158.2 g of ethyl lactate were used to obtain 54.6 g of a polymer comprising a repeating unit of formula 2 g (88.9% yield, Mw=3,600, PD=2.04).

Synthesis Example 7

Synthesis of Polymer Comprising Repeating Unit of Formula 2h

The procedures were performed in the same manner as described in Synthesis Example 1, excepting that 30 g (0.154 mole) of acridone and 54.15 g (0.338 mole) of 1,6-dihydroxynaphthalene in combination with 150.72 g (1.537 mole) of sulfuric acid as an acid catalyst were used rather than 30 g (0.165 mole) of benzophenone and 40 g (0.362 mole) of resorcinol to prepare 67.4 g (91.5% yield) of a monomer, and that 65 g (0.136 mole) of the monomer, 0.61 g (0.007 mole) of oxalic acid, 22 g (0.271 mole) of 37% formalin, and 172.1 g of ethyl lactate were used to obtain 57.3 g of a polymer comprising a repeating unit of formula 2h (86.0% yield, Mw=3,400, PD=1.98).

Synthesis Example 8

Synthesis of Polymer Comprising Repeating Unit of Formula 2i

The procedures were performed in the same manner as described in Synthesis Example 1, excepting that 20 g (0.094 mole) of 9-fluorenone and 43.59 g (0.207 mole) of 4,9-dihydroxyphenanthracene in combination with 92.45 g (0.943 mole) of sulfuric acid as an acid catalyst were used rather than 30 g (0.165 mole) of benzophenone and 40 g (0.362 mole) of resorcinol to prepare 46.8 g (87.9% yield) of a monomer, and that 40 g (0.071 mole) of the monomer, 0.32 g (0.004 mole) of oxalic acid, 11.5 g (0.142 mole) of 37% formalin, and 104.6 g of ethyl lactate were used to obtain 36.4 g of a polymer comprising a repeating unit of formula 2i (89.1% yield, Mw=3,800, PD=2.16).

Synthesis Example 9

Synthesis of Polymer Comprising Repeating Unit of Formula 2m

The procedures were performed in the same manner as described in Synthesis Example 1, excepting that 35 g (0.165 mole) of 9-fluorenone and 51.62 g (0.363 mole) of 1,3-benzenedithiol in combination with 161.78 g (0.943 mole) of sulfuric acid as an acid catalyst were used rather than 30 g (0.165 mole) of benzophenone and 40 g (0.362 mole) of resorcinol to prepare 59.4 g (87.3% yield) of a monomer, and that 55 g (0.133 mole) of the monomer, 0.60 g (0.007 mole) of oxalic acid, 21.64 g (0.267 mole) of 37% formalin, and 148.4 g of ethyl lactate were used to obtain 53.4 g of a polymer comprising a repeating unit of formula 2m (88.1% yield, Mw=3,100, PD=1.85).

Synthesis Example 10

Synthesis of Polymer Comprising Repeating Unit of Formula 2n

The procedures were performed in the same manner as described in Synthesis Example 1, excepting that 25 g (0.118 mole) of 9-fluorenone and 49.82 g (0.259 mole) of naphthalene-1,6-dithiol in combination with 115.5 g (1.178 mole) of sulfuric acid as an acid catalyst were used rather than 30 g (0.165 mole) of benzophenone and 40 g (0.362 mole) of resorcinol to prepare 54.2 g (89.8% yield) of a monomer, and that 50 g (0.098 mole) of the monomer, 0.44 g (0.005 mole) of oxalic acid, 15.83 g (0.195 mole) of 37% formalin, and 131.4 g of ethyl lactate were used to obtain 46.8 g of a polymer comprising a repeating unit of formula 2n (91.5% yield, Mw=2,900, PD=1.76).

Synthesis Example 11

Synthesis of Polymer Comprising Repeating Unit of Formula 2p

The procedures were performed in the same manner as described in Synthesis Example 1, excepting that 25 g (0.118 mole) of thioxanthone and 49.83 g (0.259 mole) of naphthalene-1,6-dithiol in combination with 115.51 g (1.178 mole) of sulfuric acid as an acid catalyst were used rather than 30 g (0.165 mole) of benzophenone and 40 g (0.362 mole) of resorcinol to prepare 56.7 g (84.4% yield) of a monomer, and that 50 g (0.092 mole) of the monomer, 0.41 g (0.005 mole) of oxalic acid, 14.90 g (0.184 mole) of 37% formalin, and 130.5 g of ethyl lactate were used to obtain 45.8 g of a polymer comprising a repeating unit of formula 2p (89.6% yield, Mw=3,200, PD=1.83).

Examples 1 to 11

Preparation and Evaluation of Resist Under-Layer

Figure 3:
FIGS. 3 and 4 are field emission scanning electron microscopic (FE-SEM) images of silicon wafers having an etched ISO pattern coated with the resist under-layer compositions according to Example 1 of the present invention and Comparative Example 1, respectively.

Each of the polymers synthesized in Synthesis Examples 1 to 11 was dissolved in propylene glycol monomethyl ether acetate (PGMEA) at a weight ratio of 9%, and the resultant solution was filtered out through a 0.45 μm filter to obtain a resist under-layer composition. The resist under-layer composition thus obtained was applied on a silicon wafer by spin coating and baked (heated) at 350° C. for 60 seconds to prepare a film (i.e., a resist under-layer) having a thickness of 3,000 Å. For measurement of the solubility of the cross-linked film (i.e., the resist under-layer) to evaluate the cross-linking performance of the resist under-layer, the cross-linked film was immersed in an ethyl lactate solution for one minute, washed with distilled water to completely eliminate ethyl lactate, baked on a hot plate at 100° C. for 10 seconds, and then measured in regard to the thickness. To evaluate the gap-filling performance after the coating step, the resist under-layer composition was applied on a silicon wafer etched into a pattern and then baked at 350° C. for 60 seconds in the curing step. Then, the cross-section of the wafer was observed with a field emission scanning electron microscope (FE-SEM) (Hitachi S-4200®) to evaluate the gap-filling performance. To evaluate the thermal resistance of the resist under-layer, a test sample was scraped off the wafer coated with the cross-linked film and then subjected to the thermogravimetric analysis (TGA) to measure the weight loss (wt. %) at 500° C. and to the thermo desorption system (TDS) to measure the out-gassing rate. The etching selectivity was determined as the thickness (A) of the film etched per unit time (sec) under the silicon etching conditions (Si etching) and the carbon etching conditions (C etching) of a wafer coated in a same thickness. The refractive index (n-value) and the light absorption coefficient (k-value) of the resist under-layer at wavelengths of 248 nm and 193 nm were measured with a spectroscopic ellipsometer (manufactured by J. A. Woollam Co., Inc.). The evaluation results are presented in Tables 1, 2 and 3. FIG. 1 shows the TGA graph of the under-layer sample (i.e., the polymer comprising a repeating unit of formula 2a, as a cross-linking agent) according to Example 1; and FIG. 3 shows the FE-SEM image of a silicon wafer with an etched ISO pattern as coated with the resist under-layer composition according to Example 1.

Comparative Example 1

Preparation and Evaluation of Resist Under-Layer

Figure 2:
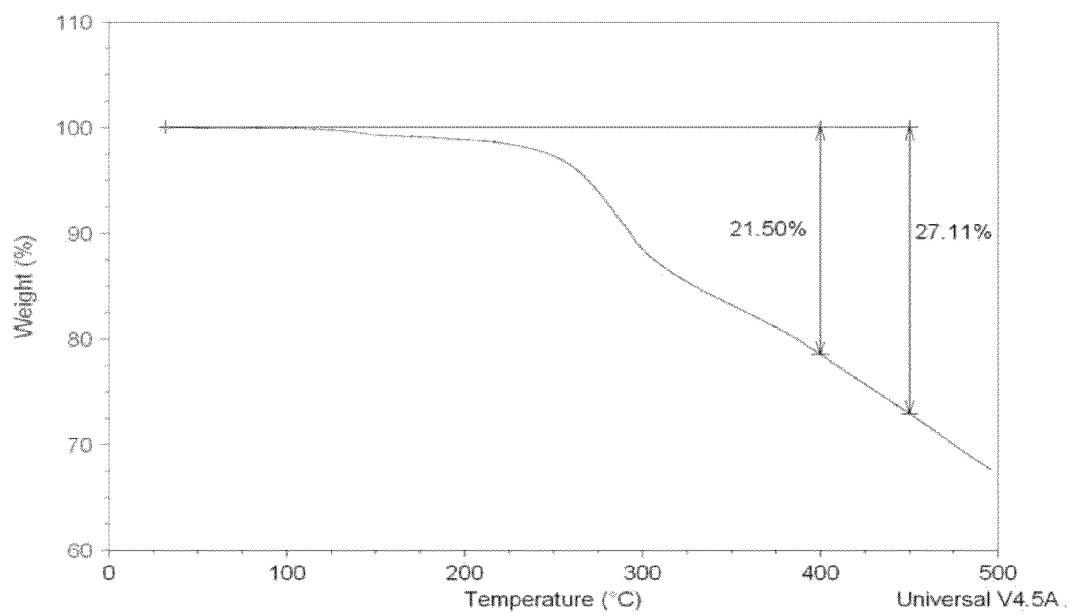
Figure 4:
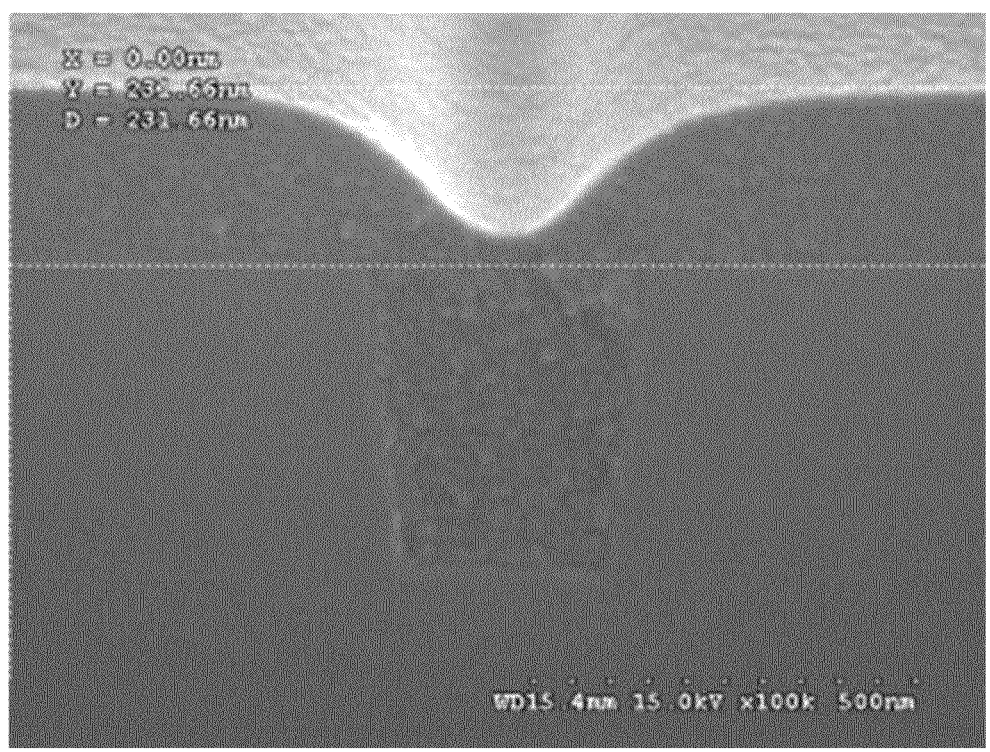

The procedures were performed in the same manner as described in Example 1 to prepare and evaluate a resist under-layer, excepting that the resist under-layer was prepared by dissolving an m-cresol novolac resin (weight average molecular weight (Mw)=3,300, polydispersity (PD)=3.5) rather than the polymers of Synthesis Examples 1 to 11 in PGMEA at a weight ratio of 9% and then adding 7 parts by weight of a cross-linking agent (MX-270® manufactured by Sanwa Chemical Co., Ltd.) and 5 parts by weight of an acid generator (K-Pure TAG-2700® manufactured by King Industries, Inc.) with respect to 100 parts by weight of the resist under-layer composition. The evaluation results are presented in Tables 1, 2 and 3. FIG. 2 shows the TGA graph of the under-layer sample (i.e., the m-cresol novolac resin, as a cross-linking agent) according to Comparative Example 1; and FIG. 4 shows the FE-SEM image of a silicon wafer with an etched ISO pattern as coated with the resist under-layer composition according to Comparative Example 1.

Comparative Example 2

Preparation and Evaluation of Resist Under-Layer

The procedures were performed in the same manner as described in Comparative Example 1 to prepare and evaluate a resist under-layer, excepting that a polyhydroxy styrene resin (weight average molecular weight (Mw)=4,800, polydispersity (PD)=1.95) was used rather than the n-cresol novolac resin. The evaluation results are presented in Tables 1, 2 and 3.

Comparative Example 3

Preparation and Evaluation of Resist Under-Layer

The procedures were performed in the same manner as described in Comparative Example 1 to prepare and evaluate a resist under-layer, excepting that a cross-linking agent and an acid generator were used. The evaluation results are presented in Tables 1, 2 and 3.

Comparative Example 4

Preparation and Evaluation of Resist Under-Layer

The procedures were performed in the same manner as described in Comparative Example 2 to prepare and evaluate a resist under-layer, excepting that a cross-linking agent and an acid generator were used. The evaluation results are presented in Tables 1, 2 and 3.

TABLE 1

| | Polymer | Acid generator | Cross-linking agent | Film variance (ΔÅ) |
|---|---|---|---|---|
| Example 1 | Synthesis Example 1 | — | — | 6 |
| Example 2 | Synthesis Example 2 | — | — | 5 |
| Example 3 | Synthesis Example 3 | — | — | 3 |
| Example 4 | Synthesis Example 4 | — | — | 7 |
| Example 5 | Synthesis Example 5 | — | — | 2 |
| Example 6 | Synthesis Example 6 | — | — | 3 |
| Example 7 | Synthesis Example 7 | — | — | 2 |
| Example 8 | Synthesis Example 8 | — | — | 4 |
| Example 9 | Synthesis Example 9 | — | — | 6 |
| Example 10 | Synthesis Example 10 | — | — | 2 |
| Example 11 | Synthesis Example 11 | — | — | 2 |
| Comparative Example 1 | Novolac resin | TAG-2700 | MX-270 | 6 |
| Comparative Example 2 | Polyhydroxy styrene resin | TAG-2700 | MX-270 | 4 |
| Comparative Example 3 | Novolac resin | — | — | 2842 |
| Comparative Example 4 | Polyhydroxy styrene resin | — | — | 2980 |

TABLE 2

| | Polymer | TGA (Weight loss at 500° C., wt %) | TDS (μg/m³) | Etching rate (Å/sec) Si etching | Etching rate (Å/sec) C etching |
|---|---|---|---|---|---|
| Example 1 | Synthesis Example 1 | 4.2 | 7,830 | 41.2 | 113.2 |
| Example 2 | Synthesis Example 2 | 3.3 | 6,972 | 39.2 | 105.7 |
| Example 3 | Synthesis Example 3 | 1.1 | 3,185 | 32.6 | 74.8 |
| Example 4 | Synthesis Example 4 | 3.6 | 7,189 | 38.6 | 99.4 |
| Example 5 | Synthesis Example 5 | 1.6 | 3,285 | 36.2 | 78.2 |
| Example 6 | Synthesis Example 6 | 1.5 | 3,351 | 35.3 | 76.7 |
| Example 7 | Synthesis Example 7 | 1.2 | 3,813 | 35.9 | 79.3 |
| Example 8 | Synthesis Example 8 | 1.1 | 2,985 | 33.4 | 102.6 |
| Example 9 | Synthesis Example 9 | 3.4 | 7,351 | 42.2 | 102.1 |
| Example 10 | Synthesis Example 10 | 1.3 | 3,115 | 31.7 | 76.6 |
| Example 11 | Synthesis Example 11 | 1.2 | 3,252 | 32.1 | 77.6 |
| Comparative Example 1 | Novolac resin | 76.2 | 44,133 | 34.6 | 40.6 |
| Comparative Example 2 | Polyhydroxy styrene resin | 78.7 | 38,246 | 33.7 | 98.5 |
| Comparative Example 3 | Novolac resin | 81.9 | N/A | 40.6 | 38.9 |
| Comparative Example 4 | Polyhydroxy styrene resin | 82.6 | N/A | 39.74 | 97.8 |

TABLE 3

| | | 193 nm | | 248 nm | |
|---|---|---|---|---|---|
| | Polymer | Refractive index n | Light absorption coefficient k | Refractive index n | Light absorption coefficient k |
| Example 1 | Synthesis Example 1 | 1.34 | 0.49 | 1.72 | 0.38 |
| Example 2 | Synthesis Example 2 | 1.41 | 0.53 | 1.81 | 0.43 |
| Example 3 | Synthesis Example 3 | 1.46 | 0.46 | 1.87 | 0.67 |
| Example 4 | Synthesis Example 4 | 1.47 | 0.45 | 1.78 | 0.57 |
| Example 5 | Synthesis Example 5 | 1.48 | 0.47 | 1.84 | 0.64 |
| Example 6 | Synthesis Example 6 | 1.50 | 0.46 | 1.83 | 0.63 |
| Example 7 | Synthesis Example 7 | 1.47 | 0.45 | 1.79 | 0.72 |
| Example 8 | Synthesis Example 8 | 1.37 | 0.48 | 1.86 | 0.84 |
| Example 9 | Synthesis Example 9 | 1.67 | 0.41 | 1.89 | 0.67 |
| Example 10 | Synthesis Example 10 | 1.64 | 0.46 | 1.88 | 0.71 |
| Example 11 | Synthesis Example 11 | 1.71 | 0.47 | 1.92 | 0.74 |
| Comparative Example 1 | Novolac resin | 1.42 | 0.57 | 1.72 | 0.33 |
| Comparative Example 2 | Polyhydroxy styrene resin | 1.54 | 0.53 | 1.82 | 0.36 |

As can be seen from the evaluation results, the resist under-layer composition according to the present invention forms a hard mask (i.e., a spin-on-carbon (SOC) hard mask) by spin coating, exerts the self-crosslinking property without an additive such as a cross-linking agent at high temperature and has a low out-gassing rate in the subsequent step of heating up to 400° C., consequently with usefulness as a high-temperature SOC material. Furthermore, the under-layer composition of the present invention is excellent in thermal stability and optical properties and improved in etching resistance (i.e., etching selectivity). As can be seen from FIGS. 1 to 4, the under-layer composition of the present invention has a high gap-filling performance and provides good smoothness when applied to a wafer having a height difference.

FIG. 4 is a section view showing a state where the auxiliary container is located on the ground or the floor according to another preferred embodiment of the present invention.

FIG. 5 is a perspective view showing a modification of the coupling means, and FIGS. 6a and 6b are plan sectional views showing a coupled state of the coupling means of FIG. 5.

The coupling means 10 for coupling the main container 4 and the auxiliary container 5 with each other includes a convex portion 4a formed on the bottom of the main container 4 and a concave portion 5a formed on the bottom of the auxiliary container 5, the convex portion 4a having upwardly opened indentations 13 opposed to each other and guide grooves 14 formed on lower portions of the indentations 13 in a clockwise direction or a counterclockwise direction in such a way that their diameters are gradually increased, the concave portion 5a having fixing projections 15 formed on an inner circumferential surface thereof in such a way as to move along the guide grooves 14 in a state where the fixing projections 15 are respectively inserted into the indentations 13, whereby the main container 4 and the auxiliary container 5 are coupled with each other.

That is, as shown in FIG. 6a, in the state where the fixing projections 15 are inserted into the indentations 13, when a user rotates the main container 4 and the auxiliary container 5 in opposite directions to each other, the fixing projections 15 move along the guide grooves 14, which are gradually increased in diameter. After that, as shown in FIG. 6b, the fixing projections 15 are in close contact with bottoms of the guide grooves 14 to thereby couple the main container 4 and the auxiliary container 5 with each other.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. A polymer for preparing a resist under-layer, comprising a repeating unit represented by the following formula 2:

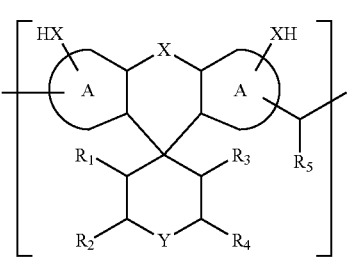

Formula 2 wherein $R_1$, $R_2$, $R_3$, $R_4$ and $R_5$ are independently a hydrogen atom, or a straight-chain, branched, monocyclic or polycyclic saturated or unsaturated hydrocarbon group having 1 to 20 carbon atoms with or without a hetero atom;

A is a monocyclic or polycyclic aromatic hydrocarbon group having 4 to 20 carbon atoms;

X is an oxygen atom (O) or a sulfur atom (S); and

Y is a single bond, a methylene group (—CH$_2$—), an oxygen atom (O), a sulfur atom (S), an amino group (—NH—), or two isolated hydrogen atoms, wherein A, $R_1$, $R_2$, $R_3$, and $R_4$ can be substituted with a straight-chain, branched, monocyclic or polycyclic saturated or unsaturated hydrocarbon group having 1 to 20 carbon atoms with or without a hetero atom; and either $R_1$ and $R_2$ or $R_3$ and $R_4$ are independently linked to each other to form a ring.

2. The polymer as claimed in claim 1, wherein polymer for preparing a resist under-layer, comprising a repeating unit represented by the formula 2 is selected from a group consisting of polymer containing a repeating unit represented by following Formula 2a to 2q,

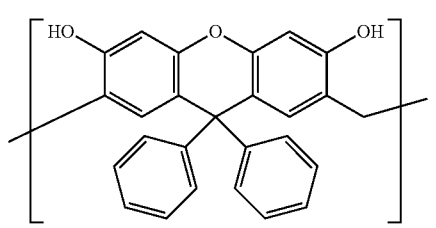

Formula 2a

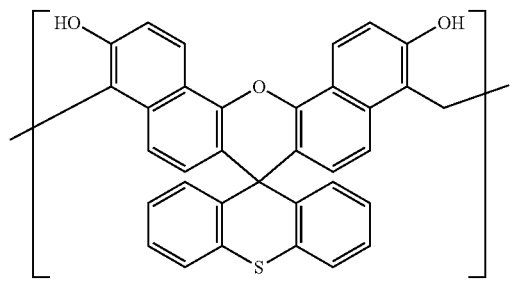

Formula 2b

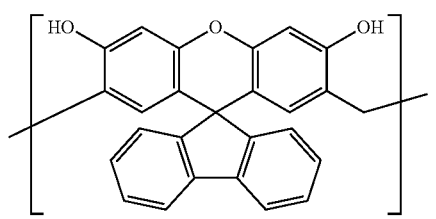

Formula 2c

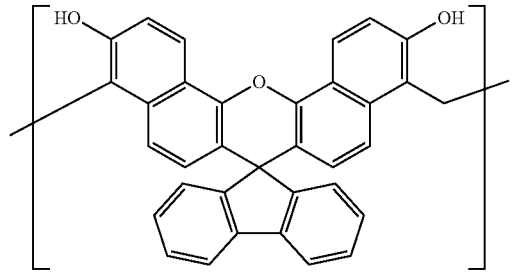

Formula 2d

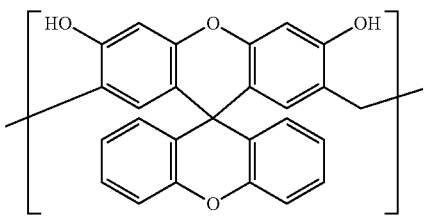

Formula 2e

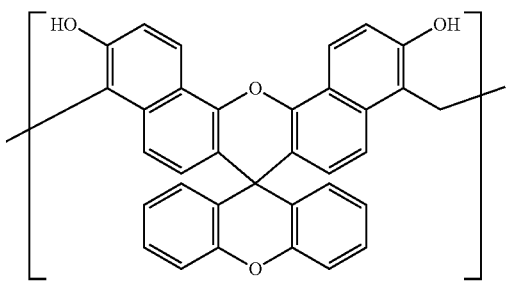

Formula 2f

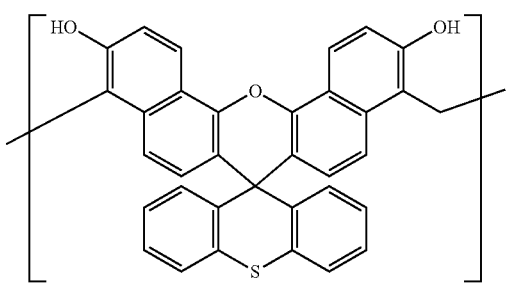

Formula 2g

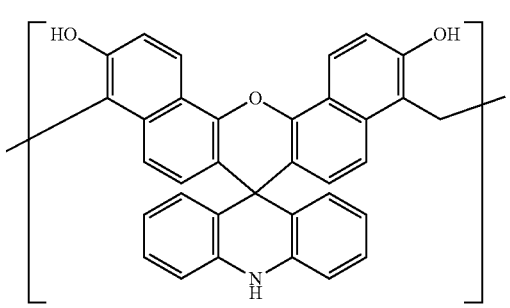

Formula 2h

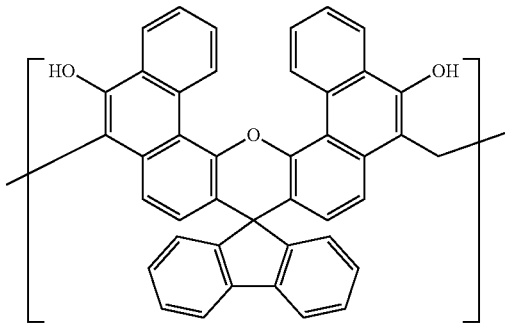

Formula 2i

Formula 2j
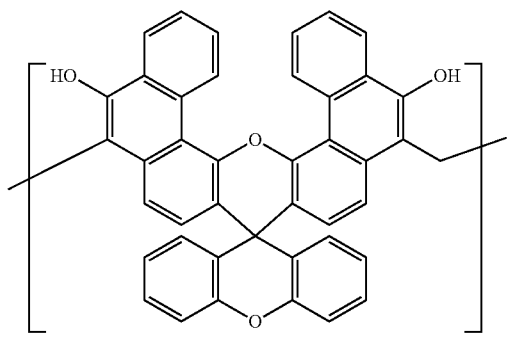

Formula 2k
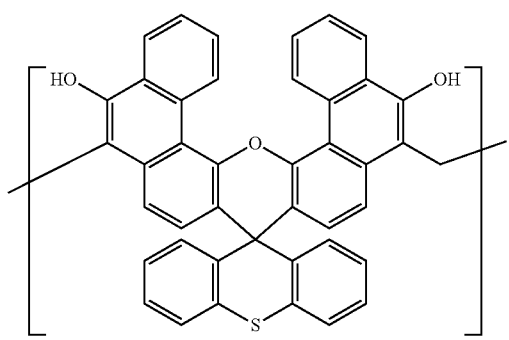

Formula 2l
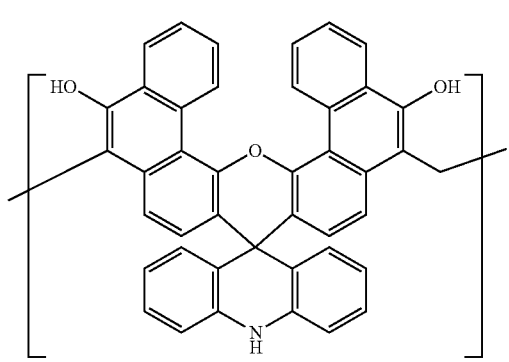

Formula 2m
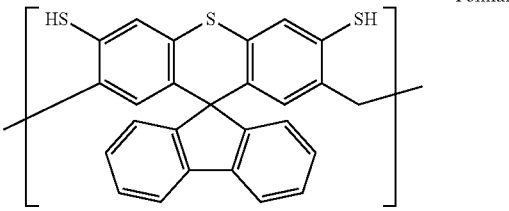

Formula 2n
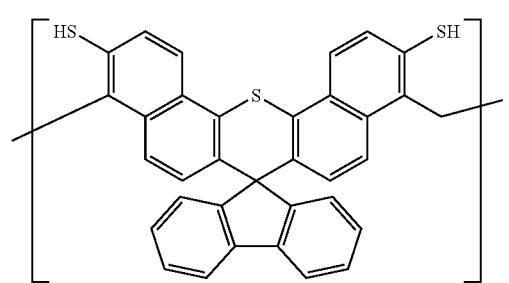

Formula 2o
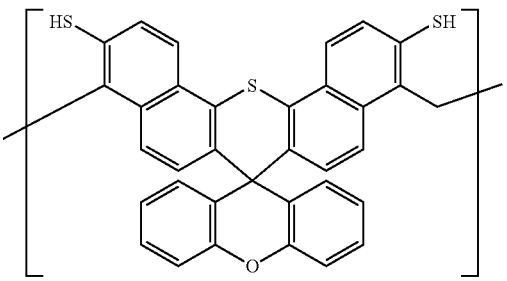

Formula 2p
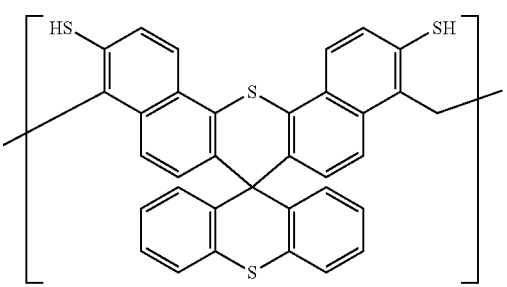

Formula 2q
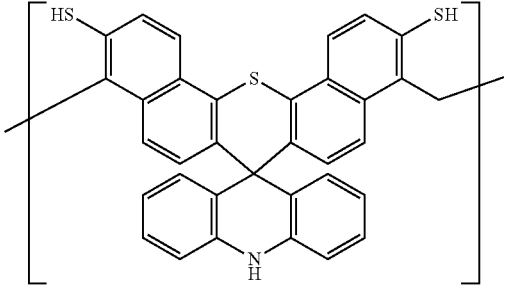

3. The polymer as claimed in claim 1, wherein a weight average molecular weight Mw of the polymer for preparing a resist under-layer is 500 to 20,000.

4. A resist under-layer composition comprising:
a polymer for preparing a resist under-layer, the polymer comprising a repeating unit represented by the following formula 2; and
an organic solvent, Formula 2
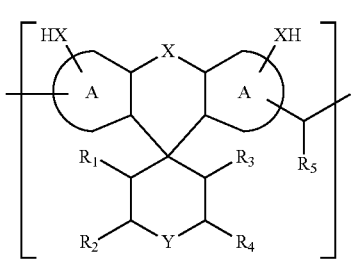

wherein $R_1$, $R_2$, $R_3$, $R_4$ and $R_5$ are independently a hydrogen atom, or a straight-chain, branched, monocyclic or polycyclic saturated or unsaturated hydrocarbon group having 1 to 20 carbon atoms with or without a hetero atom;

A is a monocyclic or polycyclic aromatic hydrocarbon group having 4 to 20 carbon atoms;

X is an oxygen atom (O) or a sulfur atom (S); and

Y is a single bond, a methylene group (—CH$_2$—), an oxygen atom (O), a sulfur atom (S), an amino group (—NH—), or two isolated hydrogen atoms, wherein A, R$_1$, R$_2$, R$_3$, and R$_4$ can be substituted with a straight-chain, branched, monocyclic or polycyclic saturated or unsaturated hydrocarbon group having 1 to 20 carbon atoms with or without a hetero atom; and either R$_1$ and R$_2$ or R$_3$ and R$_4$ are independently linked to each other to form a ring.

5. The resist under-layer composition as claimed in claim 4, wherein the organic solvent is selected from a group consisting of propylene glycol monomethyl ether acetate (PGMEA), propylene glycol monomethyl ether (PGME), cyclohexaneone (CH), ethyl lactate (EL), gamma-butyrolactone (GBL) and mixtures thereof.

6. The resist under-layer composition as claimed in claim 4, wherein the content of the polymer for preparing a resist under-layer is 1 to 25 wt. %, and the content of the organic solvent is the remainder.

7. A patterning method comprising:
(a) forming a resist under-layer on the top of a substrate to be etched, by using a resist under-layer composition comprising a polymer for forming a resist under-layer;
(b) forming a photoresist layer on the top of the resist under-layer;
(c) exposing the photoresist layer to radioactive radiation into a defined pattern to form a pattern having an exposed region in the photoresist layer;
(d) selectively removing the photoresist layer and the resist under-layer according to the pattern to expose the substrate in accordance with the pattern; and
(e) etching the exposed portion of the substrate,
wherein the polymer for forming a resist under-layer comprises a repeating unit represented by the following formula 2:

Formula 2

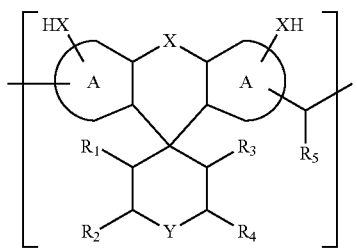

wherein R$_1$, R$_2$, R$_3$, R$_4$ and R$_5$ are independently a hydrogen atom, or a straight-chain, branched, monocyclic or polycyclic saturated or unsaturated hydrocarbon group having 1 to 20 carbon atoms with or without a hetero atom;

A is a monocyclic or polycyclic aromatic hydrocarbon group having 4 to 20 carbon atoms;

X is an oxygen atom (O) or a sulfur atom (S); and

Y is a single bond, a methylene group (—CH$_2$—), an oxygen atom (O), a sulfur atom (S), an amino group (—NH—), or two isolated hydrogen atoms, wherein A, R$_1$, R$_2$, R$_3$, and R$_4$ can be substituted with a straight-chain, branched, monocyclic or polycyclic saturated or unsaturated hydrocarbon group having 1 to 20 carbon atoms with or without a hetero atom; and either R$_1$ and R$_2$ or R$_3$ and R$_4$ are independently linked to each other to form a ring.

8. The patterning method as claimed in claim 7, wherein the step of forming the resist under-layer comprises:

applying the resist under-layer composition onto the top of the substrate to have a thickness of 500 to 6,000 Å by spin coating; and heating at 240 to 400° C. for 50 to 180 seconds, wherein the resist under-layer has a thickness of 40 to 550 nm.

9. The patterning method as claimed in claim 7, wherein the step of removing the resist under-layer is carried out by dry etching with a CHF$_3$/CF$_4$ mixed gas.

10. The patterning method as claimed in claim 7, wherein the organic solvent is selected from a group consisting of propylene glycol monomethyl ether acetate (PGMEA), propylene glycol monomethyl ether (PGME), cyclohexaneone (CH), ethyl lactate (EL), gamma-butyrolactone (GBL) and mixtures thereof.

11. The patterning method as claimed in claim 7, wherein the content of the polymer for preparing a resist under-layer is 1 to 25 wt. %, and the content of the organic solvent is the remainder.

* * * * *